United States Patent [19]
Shinto et al.

[11] Patent Number: 5,674,726
[45] Date of Patent: Oct. 7, 1997

[54] ENZYME STABILIZATION WITH POLY-L-LYSINE

[75] Inventors: Toru Shinto, Tokyo; Jun Hiraki, Yokohama, both of Japan

[73] Assignee: Chisso Corporation, Ohsaka-fu, Japan

[21] Appl. No.: 338,269

[22] Filed: Nov. 14, 1994

Related U.S. Application Data

[63] Continuation of Ser. No. 156,007, Nov. 23, 1993, abandoned.

[30] Foreign Application Priority Data

Nov. 25, 1992 [JP] Japan .................. 4-338007
Nov. 26, 1992 [JP] Japan .................. 4-339672

[51] Int. Cl.$^6$ .................. A61L 38/00; C12N 4/96
[52] U.S. Cl. .................. 435/188; 435/183; 435/193; 435/195; 435/209; 435/233; 530/300; 530/324; 530/332
[58] Field of Search .................. 435/188, 183, 435/193, 195, 209, 233; 530/300, 324, 332

[56] References Cited

U.S. PATENT DOCUMENTS

| | | | |
|---|---|---|---|
| 1,820,957 | 1/1931 | Wallerstein | 435/188 |
| 2,128,605 | 8/1938 | Dawson | 435/188 |
| 4,043,872 | 8/1977 | Blakemore et al. | 435/7.9 |
| 4,389,395 | 6/1983 | Lerner et al. | 424/85 |
| 4,443,365 | 4/1984 | Sonahara et al. | 435/188 |
| 4,582,792 | 4/1986 | Kasahara et al. | 435/7 |
| 4,675,292 | 6/1987 | Houtchens et al. | 435/188 |
| 4,769,216 | 9/1988 | Chandler et al. | 435/188 |
| 4,803,224 | 2/1989 | Tenmyo et al. | 514/563 |
| 4,927,752 | 5/1990 | Remacle | 435/8 |
| 4,933,185 | 6/1990 | Wheatley et al. | 424/461 |

FOREIGN PATENT DOCUMENTS

| | | |
|---|---|---|
| 351162 | 7/1989 | European Pat. Off. . |
| 501373 | 2/1992 | European Pat. Off. . |
| 61-243010 | 10/1986 | Japan . |
| 1120298 | 6/1967 | United Kingdom . |

OTHER PUBLICATIONS

"Sanitation of a Biocatalytic Reactor Used for Hydrolysis of Acid Whey"; *Journal of Food Science*; vol. 40, pp. 291–296 (©1975).
Gratecos et al., Biochemistry, vol. 16, No. 22, 1977.
Tanaka et al., J. Biol. Chem., vol. 261, No. 324, 15197–15203, 1986.
Shima et al. *J. of Antibiotics* 37(11), pp. 1449–145, 1984.

*Primary Examiner*—Blaine Lankford
*Attorney, Agent, or Firm*—Fay, Sharpe, Beall, Fagan, Minnich & McKee

[57] ABSTRACT

An enzyme reaction stabilizer consisting of poly-L-lysine or its salt as an effective constituent, a method for using the enzyme reaction stabilizer, and an enzyme preservative consisting of poly-L-lysine or its salt as an effective constituent are disclosed in this invention. While enzyme reactions are carried out, the enzyme reaction stabilizer and the method for using it prevents both the deactivation of enzymes due to the proliferation of included microorganisms and the decomposition of the reaction products and there is an advantage in that the enzyme reaction stabilizer can easily be separated from the reaction products. On the other hand, while the enzyme solution is preserved, the enzyme preservative of this invention prevents the deactivation of the enzyme due to the proliferation of included microorganisms in the enzyme solution or the enzyme preserving solution. Even though the enzyme solution or the enzyme preserving solution may be supplied to the enzyme reactions, the enzyme reactions are not inhibited at all. The enzyme preservative of the present invention can easily be separated and removed from the reaction products.

6 Claims, No Drawings

ENZYME STABILIZATION WITH POLY-L-LYSINE

This is a continuation of application Ser. No. 156,007 filed on Nov. 23, 1993 now abandoned.

BACKGROUND OF THE INVENTION

1. Field of the Invention

The present invention relates to an enzyme reaction stabilizer used for stably effecting an enzyme reaction and producing useful substances stably when they are produced through the enzyme reaction. Specifically, it relates to an enzyme reaction stabilizer containing poly-L-lysine or its salt as an effective constituent. More specifically, it relates to an enzyme reaction stabilizer for preventing the deactivation of the enzyme by the proliferation of microorganisms included in the enzyme reaction involving the purification process for enzyme reaction products, and the degradation of the enzyme reaction products; and for effecting the enzyme reaction stably.

Furthermore, the present invention relates to an enzyme preservative used for preserving enzymes stably. Specifically, it relates to an enzyme preservative containing poly-L-lysine or its salt as an effective constituent. More specifically, it relates to an enzyme preservative for preventing the deactivation of the enzyme by the proliferation of microorganisms included both in the enzyme solution and in the enzyme preservating solution.

2. Description of the Prior Art

In the case of producing useful substances by enzyme reactions, it has been known that the deactivation of enzymes and the degradation of reaction products are caused since various microorganisms are mixed in reaction solutions and proliferated. In the prior art, therefore, there has been a known method which uses a thermostable amylase. Even though the enzyme reaction may be conducted in the presence of the thermostable amylase at 60° C., however, it would be difficult to suppress the proliferation of thermophilic microorganisms completely, and insufficient to prevent the deactivation of the enzyme during the reaction and the degradation of reaction products. Further, after the enzyme reaction is completed, the resulting enzyme reaction solution is cooled in order to purify the reaction products. There are raised problems, however, that thermoduric spores proliferate during this time and the reaction products are decomposed at the separation and purification stages of the reaction products to make it impossible to obtain required useful substances stably and with high yields.

On the other hand, while antibiotics and antibacterial agents are known in the prior art, most of them function as enzyme inhibitors in enzyme reactions, and there are disadvantages in that they damage their enzyme reactions so that any useful substances cannot be produced, and that the above agents cannot easily be separated from the reaction products when the above agents are separated from the reaction solutions after the enzyme reactions are completed. Further, a method using lysozyme has also been known, but this method, too, has some disadvantages in that its stabilizing effect is insufficient, lysozyme is the deactivated by high temperatures in the reaction and its separation from the reaction products is difficult, etc. Thus, an enzyme reaction stabilizer having a sufficient stabilizing effect has not yet been known at present.

In the case of preserving an enzyme-dissolved solution, the deactivation of the enzyme is caused since various microorganisms are included in the enzyme solution and proliferated therein. Therefore, the enzyme solution is preserved at low temperatures of 2°–4° C., but even in that case, as a matter of fact, it cannot be preserved for a long period of time. Furthermore, for the preservation of immobilized enzymes, there has been a known method which adds antibiotics or antibacterial agents to the immobilized enzyme preserving solution. These antibiotics or antibacterial agents are, however, mostly used as an enzyme inhibitor for enzyme reactions. Therefore, it is often the case that each enzyme reaction itself is inhibited to make it impossible to produce useful substances. In such a case, it is necessary to remove these antibiotics or antibacterial agents before the enzyme reactions are conducted. As an antibacterial agent normally used, there has been known sodium azide, which is, however, a noxious gas to human bodies, and it becomes necessary to remove sodium azide completely from the reaction products at the separation and formation stages even though the enzyme reaction may not be inhibited. Due to the operation for removing sodium azide, the reduction in the yields of the reaction products is often caused as well. Thus, there have not yet been any known enzyme preservatives for satisfying the condition that has a sufficient preservation effect as an enzyme preservative with safety and without inhibiting the enzyme reactions.

SUMMARY OF THE INVENTION

As described above, it has been desired to get such an enzyme reaction stabilizer as to prevent the enzyme deactivation by the proliferation of included microorganisms, while preventing the decomposition of the reaction products, and easily separate from the reaction products.

It is accordingly a main object of this invention to solve these subjects, prevent the reaction inhibition by the proliferation of microorganisms included in enzyme reactions, enable stable enzyme reactions and provide such enzyme reaction stabilizers as to be easily separated from the reaction products.

One aspect of the present invention resides in an enzyme reaction stabilizer containing poly-L-lysine or its salt as an effective constituent and a method for using the enzyme reaction stabilizer.

The enzyme reaction stabilizer of the present invention is effected by adding it to an enzyme reaction solution when an enzyme reaction is carried out.

Another aspect of the present invention resides in an an enzyme preservative containing poly-L-lysine or its salt as an effective constituent and a method for using the enzyme preservative in the case of preserving the enzyme in the enzyme solution and in an enzyme preserving solution.

The enzyme preservative of the present invention has an effect by adding the enzyme preservative to an enzyme solution or an enzyme preserving solution in the case of preserving the enzyme in the enzyme solution or in the enzyme preserving solution. The enzyme preservative of the present invention can also suppress the proliferation of microorganisms included in an enzyme reaction by remaining the enzyme preservative in the enzyme reaction. Since the enzyme preservative of the present invention does not inhibit the enzyme reaction, there is no need of removing the enzyme preservative prior to the reaction.

The enzyme reaction stabilizer and the enzyme preservative of the present invention can be used for the enzyme reactions which use the enzymes, such as amylase, cellulase, invertase, pectinase, xylose isomerase, cyclodextrin glucosyltransferase, etc.

The enzyme reaction stabilizer of the invention can be used not only in an enzyme reaction which uses each of the above-mentioned enzyme solution but also in a reaction which uses an immobilized enzyme having each of the enzyme described above.

As for amylase, there are exemplified a α-amylase, β-amylase, glucoamylase, α-1,6-glucosidase, amylo-1,6-glucosidase, oligo-1,6-glucosidase, etc. 2-amylase is used in a starch liquefaction and a production of maltotriose in food industry. β-amylase is used for the production of starch syrup, the age resistance of rice cakes, baking, confectionery and the brewing of rice wine. Glucoamylase is an enzyme for degradating starch into each unit of glucose and used for producing glucose. α-1,6-glucosidase is an enzyme called as pullulanase and used for producing glucose and maltose. Amylo-1,6-glucosidase or oligo-1,6-glucosidase is an enzyme for dividing a α-1,6 bond and splitting the branched chain into side chains.

As cellulase, cellulose itself and hemicellulase are exemplified, which are used for the production of starch, the treatment of vegetables, fruits, grains or beans, the decomposition of the gum substance of coffee and the prevention of gelation in food industry. As pectinase, pectineesterase, polygalacturonase, etc. are exemplified. They are utilized for processing fruit juice, and for the production of citric acid and the process of fruits and vegetables. Xylose isomerase is an enzyme called as glucose isomerase inindustry and used for isomerizing glucose to produce its isomers. Cyclodextrin glucosyltransferase is an enzyme used for producing cyclodextrin from starch.

Invertase is also called saccharase and it is an enzyme for splitting sucrose into fructose and glucose. There are β-D-Fructofruranosidase for splitting sucrose from fructose side and α-D-Glucosidase for splitting sucrose from glucose side. β-D-Fructofruranosidase is used for the production of inverted sugar. On the other hand, α-D-Glucosidase is used for the production of inverted sugar and also reacted with maltose to produce isomaltose.

In the case of adding an enzyme reaction stabilizer of the present invention to an enzyme solution, it is desirable to add 0.001–10 wt. % of poly-L-lysine based upon the weight of the enzyme solution. In the case of adding more than 10 wt. % thereof, the reduction in the yields is often caused when the reaction products are refined after the termination of the reaction and it is uneconomical to add in excess since this stabilizing effect is saturated to gain no larger effect.

In the case of adding an enzyme preservative of the present invention to an enzyme solution or an enzyme preserving solution, it is desirable to add 0.001–10 wt. % of poly-L-lysine based upon the weight of the enzyme solution or the enzyme preserving solution. In the case of adding more than 10 wt. % of the enzyme preservative to them, the reduction in the yields is often caused when the reaction products are purified after the termination of the reaction and it is uneconomical to add excessively since the preserving effect is saturated and any improvement in the preserving effect cannot be obtained at all.

Poly-L-lysine used in the present invention can be obtained for example, according to a production process described in e.g., Japanese Patent Publication No.59-20359. That is, *Streptomyces albulus* subsp. lysinopolymerus, which are microorganisms for producing ε-poly-L-lysine belonging to Streptomyces genus, are caltivated in a medium and ε-poly-L-lysine is separated and sampled from the resulting culture.

L-lysine is an amino acid having two amino groups in one molecule. Poly-L-lysine obtained from L-lysine comprises two kinds of lysines: α-pol-L-lysine obtained generally by the condensation between amino group at α-position and carboxyl group and ε-poly-L-lysine obtained by the condensation between amino group at ε-position and carboxyl group. In this invention, it is preferable, however, from the viewpoint of safety to use ε-poly-L-lysine obtained by the production process described above.

Furthermore, in the case of carrying out enzyme reactions at higher temperatures or carrying out a steam sterilization by adding an enzyme reaction stabilizer, of the invention to a substrate solution prior to the addition of the enzyme, it is desirable to use ε-poly-L-lysine which is excellent in thermal stability.

In the present invention, poly-L-lysine can be used in its free form or in a salt form combined with an inorganic acid, such as hydrochloric, sulfuric or phosphoric acid or with an organic acid, such as acetic, propionic, fumaric, malic or citric acid. Whether poly-L-lysine may be in a free form or in a salt from combined with an inorganic or organic acid described above, there is substantially no difference in the effect as an enzyme reaction stabilizer or as an enzyme preservative. However, poly-L-lysine in a free form is more excellent in water solubility.

It would be desirable that poly-L-lysine used in the present invention has a polymerization degree of 10 or more from the stand point of the activity of inhibiting the proliferation of microorganisms. A polymerization degree of about 20 to 40 is particularly preferred in the aspects of water-solubility, the stability of the compound and the activity of inhibiting the proliferation of microorganisms.

After carrying out an enzyme reaction using an enzyme reaction stabilizer of the present invention, when the obtained reaction products are separated and purified, each conventional method corresponding to the reaction products may be used as a separation and purification process. In this case, it is desirable to carry out the removal of the enzyme reaction stabilizer of the present invention at the final period of the purification stage in order to prevent the decomposition of the reaction products due to the proliferation of microorganisms included therein. In this case, the enzyme reaction stabilizer of the invention can be easily separated by using an ion exchange resin because of its strong cationic property.

After carrying out an ezyme reaction using an enzyme as well as an enzyme solution added with an enzyme preservative of the present invention, in the case of separating and purifying the reaction products thus obtained, each conventional method corresponding to the reaction products may be used for their separation and purification. In this case, the enzyme preservative of the invention can be easily separated and removed by using an ion exchange resin, taking an advantage of the strong cationic property of the enzyme preservative of the present invention.

Referring now to the preferred embodiments of the present invention, the detailed description will be given in the following. While the embodiments of the present invention are herein disclosed, it is to be understood that the embodiments do not restrict the scope of the present invention.

EXAMPLE 1

To 1 ml of a buffer solution (pH 6.5) containing 20 mM phosphoric acid and 6.7 mM sodium chloride, 10 mg of a soluble starch were dissolved and then, 10 mg of β-amylase (Amano Pharmaceutical Corporation Ltd. product) and 0.1 mg of ε-poly-L-lysine were added and dissolved. To this solution, $10^3$ cells of *Staphylococcus aureus, Escherichia*

*coli* or *Bacillus cereus* were inoculated and allowed to react at 30° C. for 2 days. After the reaction was completed, the reaction solution was heated in a boiled water to stop the enzyme reaction and filtered by a 0.45 μm membrane filter. The quantity of maltose in the filtrate was measured by a dinitrophthallic acid method. The quantity of maltose thus obtained was 7 mg.

Comparative Example 1

To 1 ml of a buffer solution (pH 6.5) containing 20 mM phosphoric acid and 6.7 mM sodium chloride, 10 mg of a soluble starch were dissolved, and then, 10 mg of β-amylase (Amano Pharmaceutical Corporation Ltd. product) were added and dissolved. To this solution, $10^3$ cells of *Staphylococcus aureus, Escherichia coli* or *Bacillus cereus* were inoculated and allowed to react at 30° C. for 2 days. After the reaction was completed, the reaction solution was heated in a boiled water to stop the enzyme reaction and filtered by a 0.45 μm membrane filter. The quantity of maltose in the filtrate was measured by a dinitrophthallic acid method. No formation of maltose was recognized.

Then, in order to show that the above enzyme reaction stabilizer of the present invention has no enzyme reaction inhibition, the following two reference examples will be given as a reference.

Reference Example 1

To 1 ml of a buffer solution (pH 6.5) containing 20 mM phosphoric acid and 6.7 mM sodium chloride, 10 mg of a soluble starch were dissolved, and then, 10 mg of β-amylase (Amano Pharmaceutical Corporation Ltd. product) and 0.1 mg of ε-poly-L-lysine were added and dissolved. The solution was allowed to react at 30° C. for 2 days. After the reaction was completed, the reaction solution was heated in a boiled water to stop the enzyme reaction and filtered through a 0.45 μm membrane filter. The quantity of maltose in the filtrate was measured by a dinitrophthallic acid method. The quantity of maltose thus obtained was 7 mg.

Reference Example 2

To 1 ml of a buffer solution (pH 4.8) of 16 mM acetic acid, 10 mg of a soluble starch was dissolved, and 0.1 mg of α-amylase (Wako Pure Chemical Industries Ltd. product by using *Bacillus subtills*) were added and dissolved. The solution was allowed to react at 20° C. for 3 mins. After the reaction was completed, the reaction solution was heated in a boiled water to stop the enzyme reaction and filtered through a 0.45 μm membrane filter. The quantity of maltose in the filtrate was measured by a dinitrophthallic acid method. The quantity of maltose thus obtained was 3 mg.

EXAMPLE 2

To 1 ml of a buffer solution (pH 6.5) containing 20 mM phosphoric acid and 6.7 mM sodium chloride, 300 mg of maltose (Wako Pure Chemical Industries Ltd. product) were dissolved, and then, 10 mg of α-amylase (saccharification type, Seikakagaku Corporation product by using *Bacillus subtilis*) and 1 mg of ε-poly-L-lysine were added and dissolved. To this solution, $10^3$ cells of *Bacillus stearothermophilus* were inoculated and then allowed to react at 60° C. for 24 hrs. After the reaction was completed, the reaction solution was heated in a boiled water to stop the enzyme reaction, and filtered by a 0.45 μm membrane filter. The quantity of glucose in the filtrate was measured by a high speed liquid chromatographic method (column: Showa denko K.K. product #SC1011). The quantity of glucose thus obtained was 260 mg.

Comparative Example 2

To 1 ml of a buffer solution (pH 6.5) containing 20 mM phosphoric acid and 6.7 mM sodium chloride, 300 mg of maltose (Wako Pure Chemical Industries Ltd. product) were dissolved, and then, 10 mg of α-amylase (saccharification type, Seikakagaku Corporation product by using *Bacillus subtilis*) were added and dissolved. To this solution, $10^3$ cells of *Bacillus stearothermophilus* were inoculated and then allowed to react at 60° C. for 24 hrs. After the reaction was completed, the reaction solution was heated in a boiled water to stop the enzyme reaction and filtered by a 0.45 μm membrane filter. The quantity of glucose in the filtrate was measured by a high speed liquid chromatographic method (column: Showa denko K.K. product #SC1011). No formation of glucose was recognized.

Then, in order to show that this enzyme reaction stabilizer of the present invention has no enzyme reaction inhibition, the following Reference Example will be given as a reference.

Reference Example 3

To 1 ml of a buffer solution (pH 6.5) containing 20 mM phosphoric acid and 6.7 mM sodium chloride, 300 mg of maltose (Wako Pure Chemical Industries Ltd. product) were dissolved, and then, 10 mg of α-amylase (saccharification type, Seikakagaku Corporation product by using *Bacillus subtills*) and 1 mg of ε-poly-L-lysine were added and dissolved. The solution was allowed to react at 60° C. for 24 hrs. After the reaction was completed, the reaction solution was heated in a boiled water to stop the enzyme reaction, and filtered by a 0.45 μm membrane filter. The quantity of glucose in the filtrate was measured by a high speed liquid chromatographic method (column: Showa denko K.K product #SC1011). The quantity of glucose thus obtained was 265 mg.

EXAMPLE 3

To 1 ml of a buffer solution (pH 6.5) containing 20 mM phosphoric acid and 6.7 mM sodium chloride, 300 mg of maltose (Wako Pure Chemical Industries Ltd. product) were dissolved, and then, 10 mg of α-amylase (saccharification type, Seikakagaku Corporation product by using *Bacillus subtilis*) and 1 mg of ε-poly-L-lysine hydrochloride were added and dissolved. To this solution, $10^3$ cells of *Bacillus stearothermophilus* were inoculated and then, were allowed to react at 60° C. for 24 hrs. After the reaction was completed, the reaction solution was heated in a boiled water to stop the enzyme reaction, and filtered through a 0.45 μm membrane filter. The quantity of glucose in the filtrate was measured by a high speed liquid chromatographic method. The quantity of glucose thus obtained was 260 mg.

Comparative Example 3

To 1 ml of a buffer solution containing 20 mM phosphoric acid and 6.7 mM sodium chloride, 300 mg of maltose (Wako Pure Chemical Industries Ltd. product) were dissolved, and then, 10 mg of α-amylase (saccharification type, Seikakagaku Corporation product by using *Bacillus subtills*) were added and dissolved. To this solution, $10^3$ cells of *Bacillus stearothermophilus* were inoculated and then allowed to react at 60° C. for 24 hrs. After the reaction was completed, the reaction solution was heated in a boiled water to stop the enzyme reaction, and filtered through a 0.45 μm membrane filter. The quantity of glucose in the filtrate was measured by a high speed liquid chromatographic method. No formation of glucose was recognized.

Then, in order to show that this enzyme reaction stabilizer of the invention has no enzyme reaction inhibition, the following example will be given as a reference.

Reference Example 4

To 1 ml of a buffer solution containing 20 mM phosphoric acid and 6.7 mM sodium chloride, 300 mg of maltose (Wako Pure Chemical Industries Ltd. product) were dissolved, and then, 10 mg of α-amylase (saccharification type, Seikakagaku Corporation product by using *Bacillus subtilis*) and 1 mg of ε-poly-L-lysine hydrochlorate were added and dissolved. The resulting solution was allowed to react at 60° C. for 24 hrs. After the reaction was completed, the reaction solution was heated in a boiled water to stop the enzyme reaction, and filtered through a 0.45 μm membrane filter. The quantity of glucose in the filtrate was measured by a high speed liquid chromatographic method. The quantity of glucose thus obtained was 265 mg.

EXAMPLE 4

To 1 ml of a 20 mM phosphoric acid buffer solution (pH 6.5), 1 mg of cellulase (Worthington Biochemical Corp. product by using *Trichoderma reesei*, freeze-dried powder) and 0.5 mg of ε-poly-L-lysine were dissolved. To 1 ml of a 50 mM acetic acid buffer solution (pH 5.0), 0.1 ml of this solution and 10 mg of Avicel (FMC corp. product, Trademark) were added and dissolved. The spores (equivalent to $10^3$ colony-forming units) of *Bacillus subtills* were inoculated to the solution and allowed to react at 30° C. for 60 mins. After the reaction was completed, the reaction solution was heated in a boiled water to stop the enzyme reaction and then left at 30° C. for 24 hrs. This solution was filtered through a 0.45 μm membrane filter. The quantity of glucose in the filtrate was measured by a high speed liquid chromatographic method (column: Showa denko K.K. product, #SC1011). The quantity of glucose thus obtained was 5 mg.

Comparative Example 4

To 1 ml of a 20 mM phosphoric acid buffer solution (pH 6.5), 1 mg of cellulase (Worthington Biochemical Corp. product by using *Trichoderma reesei*, freeze-dried powder) was added and dissolved. To 1 ml of a 50 mM acetic acid buffer solution (pH 5.0), 0.1 ml of the above solution and 10 mg of Avicel (FMC corp. product) were added and dissolved. The spores (equivalent to $10^3$ colony-forming units) of *Bacillus subtilis* were inoculated to the solution and allowed to react at 30° C. for 60 mins. After the reaction was completed, the reaction solution was heated in a boiled water to stop the enzyme reaction and then left at 30° C. for 24 hrs. This solution was filtered through a 0.45 μm membrane filter. The quantity of glucose in the filtrate was measured by a high speed liquid chromatographic method (column: Showa denko K.K. product #SC1011). No formation of glucose was recognized.

EXAMPLE 5

To 1 ml of a 20 mM phosphoric acid buffer solution (pH 6.5), 1 mg of invertase (Funakoshi K.K. product by using Candida sp., freeze-dried powder) and 0.5 mg of ε-poly-L-lysine were added and dissolved. To 1 ml of a 50 mM acetic acid buffer solution (pH 4.6), 0.1 ml of this solution and 10 mg of sucrose (Wako Pure Chemical Industries Ltd. product) were added and dissolved. The spores (equivalent to $10^3$ colony-forming units) of *Bacillus subtills* were inoculated to the solution and allowed to react at 30° C. for 60 mins. After the reaction was completed, the reaction solution was heated in a boiled water to stop the enzyme reaction and then left at 30° C. for 24 hrs. The solution was filtered through a 0.45 μm membrane filter. The quantity of glucose in the filtrate was measured by a high speed liquid chromatographic method (column: Showa denko product, #SC1011)

The quantity of glucose thus obtained was 5 mg.

Comparative Example 5

To 1 ml of a 20 mM phosphoric acid buffer solution (pH 6.5), 1 mg of invertase (Funakoshi K.K. product from Candida sp., freeze-dried powder) was added and dissolved. To 1 ml of a 50 mM acetic acid buffer solution (pH 4.6), 0.1 ml of this solution and 10 mg of sucrose (Wako Pure Chemical Industries Ltd. product) were added and dissolved. The spores (equivalent to $10^3$ colony-forming units) of *Bacillus subtilis* were inoculated to the solution and then allowed to react at 30° C. for 60 mins. After the reaction was completed, the reaction solution was heated in a boiled water to stop the enzyme reaction and then left at 30° C. for 24 hrs. The solution was filtered through a 0.45 μm membrane filter. The quantity of glucose in the filtrate was measured by a high speed liquid chromatographic method (column: Showa denko K.K. product, #SC1011). No formation of glucose was recognized.

EXAMPLE 6

To 1 ml of a buffer solution (pH 6.5) containing 20 mM phosphoric acid and 6.7 mM sodium chloride, 10 mg of a soluble starch was dissolved, and then, 10 mg of β-amylase (Amano Pharmaceutical Corporation Ltd. product) and 0.1 mg of ε-poly-L-lysine were added and dissolved. The spores of *Bacillus cereus* (equivalent to $10^3$ colony-forming units) were inoculated to the solution and then allowed to react at 30° C. for 2 days. After the reaction was completed, the reaction solution was heated in a boiled water to stop the enzyme reaction. The solution was left at 30° C. for 24 hrs. and then filtered through a 0.45 μm membrane filter. The quantity of maltose in the filtrate was measured by a dinitrophthallic acid method. The quantity of maltose thus obtained was 7 mg.

Comparative Example 6

To 1 ml of a buffer solution (pH 6.5) containing 20 mM phosphoric acid and 6.7 mM sodium chloride, 10 mg of a soluble starch was dissolved, and then, 10 mg of β-amylase (Amano Pharmaceutical Corporation Ltd. product) were added and dissolved. The spores of *Bacillus cereus* (equivalent to $10^3$ colony-forming units) were inoculated to the solution and then allowed to react at 30° C. for 2 days. After the reaction was completed, the reaction solution was heated in a boiled water to stop the enzyme reaction. The solution was left at 30° C. for 24 hrs. and then filtered through a 0.45 μm membrane filter. The quantity of maltose in the filtrate was measured by a dinitrophthallic acid method. No formation of maltose was recognized.

EXAMPLE 7

To 1 ml of a buffer solution (pH 6.5) containing 20 mM phosphoric acid and 6.7 mM sodium chloride, 300 mg of maltose (Wako Pure Chemical Industries Ltd. product) was dissolved, and then, 10 mg of α-amylase (saccharification type, Seikakagaku Corporation product by using *Bacillus subtilis*) and 1 mg of ε-poly-L-lysine were added and dissolved. The spores of *Bacillus cereus* (equivalent to $10^3$ colony-forming units) were inoculated to the solution and allowed to react at 60° C. for 24 hrs. After the reaction was completed, the reaction solution was heated in a boiled water to stop the enzyme reaction, and filtered through a 0.45 μm membrane filter. The quantity of glucose in the filtrate was measured by a high speed liquid chromatographic method (column: Showa denko K.K. product, #SC1011). The quantity of glucose thus obtained was 260 mg.

Comparative Example 7

To 1 ml of a buffer solution (pH 6.5) containing 20 mM phosphoric acid and 6.7 mM sodium chloride, 300 mg of maltose (Wako Pure Chemical Industries Ltd. product) was dissolved, and then, 10 mg of α-amylase (saccharification type, Seikakagaku Corporation product by using. *Bacillus subtilis*) were added and dissolved. The spores of *Bacillus cereus* (equivalent to $10^3$ colony-forming units) were inoculated to this solution and then allowed to react at 60° C. for 24 hrs. After the reaction was completed, the reaction solution was heated in a boiled water to stop the enzyme reaction, and then left at 30° C. for 24 hrs. The solution was filtered through a 0.45 μm membrane filter. The quantity of glucose in the filtrate was measured by a high speed liquid chromatographic method (column: Showa denko K.K. product, #SC1011). No formation of glucose was recognized.

EXAMPLE 8

To 1 ml of a buffer solution (pH 6.5) containing 20 mM phosphoric acid and 6.7 mM sodium chloride, 10 mg of a soluble starch was dissolved, and then, 10 mg of mixture of glucoamylase and +α-1,6 glucosidase (Amano Pharmaceutical Corporation Ltd. product, "Silverase"[trade name]) and 0.1 mg of ε-poly-L-lysine were added and dissolved. The spores of *Bacillus cereus* (equivalent to $10^3$ colony-forming units) were inoculated to the solution and then allowed to react at 30° C. for 2 days. After the reaction was completed, the reaction solution was heated in a boiled water to stop the enzyme reaction and then left at 30° C. for 24 hrs. The solution was then filtered through a 0.45 μm membrane filter. The quantity of maltose in the filtrate was measured by a high speed liquid chromatographic method (column: Showa denko K.K. product, #SC1011). The quantity of glucose thus obtained was 8 mg.

Comparative Example 8

To 1 ml of a buffer solution (pH 6.5) containing 20 mM phosphoric acid and 6.7 mM sodium chloride, 10 mg of a soluble starch was dissolved, and then, 10 mg of mixture of glucoamylase and α-1,6 glucosidase (Amano Pharmaceutical Corporation Ltd. product, "Silverase"[trade name]) and 0.1 mg of ε-poly-L-lysine were added and dissolved. The spores of *Bacillus cereus* (equivalent to $10^3$ colony-forming units) were inoculated to the solution and then allowed to react at 30° C. for 2 days. After the reaction was completed, the reaction solution was heated in a boiled water to stop the enzyme reaction and then left at 30° C. for 24 hrs. The solution was filtered through a 0.45 μm membrane filter. The quantity of glucose in the filtrate was measured by a high speed liquid chromatographic method (column: Showa denko K.K. product, #SC1011). No formation of glucose was recognized.

EXAMPLE 9

To 1 ml of a buffer solution (pH 7.5) containing 20 mM phosphoric acid and 6.7 mM sodium chloride, 10 mg of a soluble starch were dissolved, and then, 1 mg of α-glucosidase (Funakoshi K.K. product) and 0.1 mg of ε-poly-L-lysine were added and dissolved. The spores of *Bacillus cereus* (equivalent to $10^3$ colony-forming units) were inoculated to the solution and then allowed to react at 30° C. for 2 days. After the reaction was completed, the reaction solution was heated in a boiled water to stop the enzyme reaction and then left at 30° C. for 24 hrs. The solution was filtered through a 0.45 μm membrane filter. The quantity of maltotriose in the filtrate was measured by a high speed liquid chromatographic method (column: Showa denko K.K. product, #SC1821). The quantity of maltotriose was 1 mg.

Comparative Example 9

To 1 ml of a buffer solution (pH 7.5) containing 20 mM phosphoric acid and 6.7 mM sodium chloride, 10 mg of a soluble starch was dissolved, and then, 1 mg of α-glucosidase (Funakoshi K.K. product) was added and dissolved. The spores of *Bacillus cereus* (equivalent to $10^3$ colony-forming units) were inoculated to the solution and then allowed to react at 30° C. for 2 days. After the reaction was completed, the reaction solution was heated in a boiled water to stop the enzyme reaction and then left at 30° C. for 24 hrs. The solution was filtered through a 0.45 μm membrane filter. The quantity of maltotriose in the filtrate was measured by a high speed liquid chromatographic method (column: Showa denko K.K. product, #SC1821). No formation of glucose was recognized.

EXAMPLE 10

To 1 ml of a buffer solution (pH 6.8) containing 20 mM phosphoric acid and 6.7 mM sodium chloride, 10 mg of glucose were dissolved, and then, 10 mg of xylose isomerase (prepared by using *Bacillus coagulans*) and 0.1 mg of ε-poly-L-lysine were added and dissolved. The spores of *Bacillus cereus* (equivalent to $10^3$ colony-forming units) were inoculated to the solution and then allowed to react at 30° C. for 2 days. After the reaction was completed, the reaction solution was heated in a boiled water to stop the enzyme reaction. The solution was left at 30° C. for 24 hrs. and then filtered through a 0.45 μm membrane filter. The quantities of fructose and glucose in the filtrate were measured by a high speed liquid chromatographic method (column: Showa denko K.K. product, #SC1011) so as to determine the content of fructose. The resulting fructose content ratio was 35%.

Comparative Example 10

To 1 ml of a buffer solution (pH 6.8) containing 20 mM phosphoric acid and 6.7 mM sodium chloride, 10 mg of glucose was dissolved, and then, 10 mg of xylose isomerase prepared by using *Bacillus coagulans*) was added and dissolved. The spores of *Bacillus cereus* (equivalent to $10^3$ colony-forming unites) were inoculated to the solution and then allowed to react at30° C. for 2 days. After the reaction was completed, the reaction solution was heated in a boiled water to stop the enzyme reaction. The solution was left at 30° C. for 24 hrs. and then filtered through a 0.45 μm membrane filter. The quantities of fructose and glucose in the filtrate were measured by a high speed liquid chromatographic method (column: Showa denko K.K. product, #SC1011). Both fructose and glucose were not detected.

EXAMPLE 11

To 50 ml of a buffer solution (pH 7.5) containing 20 mM phosphoric acid and 6.7 mM sodium chloride, 10 mg of a soluble starch were dissolved, and then 2 ml of cyclodextrin glucosyltransferase (Amano Pharmaceutical Corporation Ltd. product, 600U/ml ) and 50 mg of ε-poly-L-lysine were added and dissolved. The spores of *Bacillus cereus* (equivalent to $10^3$ colony-forming units) were inoculated to the solution and then allowed to react at 65° C. for 40 hrs. After the reaction wascompleted, the reaction solution was heated in a boiled water to stop the enzyme reaction. The solution was left at 30° C. for 24 hrs. and filtered through a 0.45 μm membrane filter. The quantity of cyclodextrin in the filtrate was measured by a high speed liquid chromatographic method (column: Showa denko K.K. product, #RSpakDC-613). The total quantity of α, β, γ-cyclodextrin thus obtained was 7 g.

Comparative Example 11

To 50 ml of a buffer solution (pH 7.5) containing 20 mM phosphoric acid and 6.7 mM sodium chloride, 10 mg of a soluble starch were dissolved, and then 2 ml of cyclodextrin glucosyltransferase (Amano Pharmaceutical Corporation Ltd. product, 600U/ml) were added and dissolved. The spores of *Bacillus cereus* (equivalent to $10^3$ colony-forming units) were inoculated to the solution and then allowed to react at 65° C. for 40 hrs. After the reaction was completed, the reaction solution was heated in a boiled water to stop the enzyme reaction. The solution was left at 30° C. for 24 hrs. and then filtered through a 0.45 μm membrane filter. The quantity of cyclodextrin in the filtrate was measured by a high speed liquid chromatographic method (column: Showa denko K.K. product, #RSpakDC-613). No formation of cyclodextrin was recognized.

EXAMPLE 12

To 10 ml of a 20 mM tris hydrochloric acid buffer solution (pH 5.0), 1 g of polygalacturonic acid (Funakoshi K.K. product) was dissolved, and then, 10 mg of pectinase (Funakoshi K.K. product by using *Aspergillus niger*, freeze-dried item) and 10 mg of ε-poly-L-lysine were added and dissolved. To this solution, $10^3$ cells of *Lactobacillus brevis* were inoculated and then allowed to react at 37° C. for 24 hrs. After the reaction was completed, the reaction solution was heated in a boiled water to stop the enzyme reaction and filtered through a 0.45 μm membrane filter. The quantity of galacturonic acid in the filtrate was measured by a high speed liquid chromatographic method (column: YMC Corp. product, #Diol-120). The quantity of galacturonic acid thus obtained was 450 mg.

Comparative Example 12

To 10 ml of a 20 mM tris hydrochloric acid buffer solution (pH 5.0), 1 g of polygalacturonic acid (Funakoshi K.K. product) was dissolved, and then, 10 mg of pectinase (Funakoshi K.K. product by using *Aspergillus niger*, freeze-dried item) were added and dissolved. Then, $10^3$ cells of *Lactobacillus brevis* were inoculated to the solution and then allowed to react at 37° C. for 24 hrs. After the reaction was completed, the reaction solution was heated in a boiled water to stop the enzyme reaction and filtered through a 0.45 μm membrane filter. The quantity of galacturonic acid in the filtrate was measured by a high speed liquid chromatographic method (column: YMC Corp. product, #Diol-120). No formation of galacturonic acid was recognized.

EXAMPLE 13

To 1 ml of a 20 mM phosphoric acid buffer solution (pH 6.5), 10 mg of α-amylase (Wako Pure Chemical Industries Ltd. product by using *Bacillus subtilis*) and 0.5 mg of ε-poly-L-lysine were added and dissolved. Then, $10^3$ cells of *Bacillus subtills* were inoculated to the solution and left at 30° C. for 24 hrs. The solution was filtered through a 0.45 μm membrane filter. To 1 ml of 16 mM acetic acid buffer solution (pH.4.8), 0.1 ml of the filtrate and 10 mg of a soluble starch were added and dissolved. This solution was allowed to react at 20° C. for 3 mins. After the reaction was completed, the reaction solution was heated in a boiled water to stop the enzyme reaction and then filtered through a 0.45 μm membrane filter. The quantity of maltose in the filtrate was measured by a dinitrophthallic acid method. The quantity of maltose thus obtained was 3 mg.

Comparative Example 13

To 1 ml of a 20 mM phosphoric acid buffer solution (pH 6.5), 10 mg of α-amylase (Wako Pure Chemical Industries Ltd. product by using *Bacillus subtilis*) were added and dissolved. Then, $10^3$ cells of *Bacillus subtilis* were inoculated to the solution and left at 30° C. for 24 hrs. The solution was filtered through a 0.45 μm membrane filter. To 1 ml of 16 mM acetic acid buffer solution (pH 4.8), 0.1 ml of the filtrate and 10 mg of a soluble starch were added and dissolved. This solution was allowed to react at 20° C. for 3 mins. After the reaction was completed, the reaction solution was heated in a boiled water to stop the enzyme reaction and then filtered through a 0.45 μm membrane filter. The quantity of maltose in the filtrate was measured by a dinitrophthallic acid method. No formation of maltose was recognized.

EXAMPLE 14

To 1 ml of a 20 mM phosphoric acid buffer solution (pH 6.5), 10 mg of α-amylase (Wako Pure Chemical Industries Ltd. product by using *Bacillus subtilis*) and 0.5 mg of ε-poly-L-lysine hydrochloride were added and dissolved. Then, $10^3$ cells of *Bacillus subtilis* were inoculated to the solution and left at 30° C. for 24 hrs. The solution was filtered through a 0.45 μm membrane filter. To 1 ml of 16 mM acetic acid buffer solution (pH 4.8), 0.1 ml of the filtrate and 10 mg of a soluble starch were dissolved. This solution was allowed to react at 20° C. for 3 mins. After the reaction was completed, the reaction solution was heated in a boiled water to stop the enzyme reaction and then filtered through a 0.45 μm membrane filter. The quantity of maltose in the filtrate was measured by a dinitrophthallic acid method. The quantity of maltose thus obtained was 3 mg.

EXAMPLE 15

To 1 ml of a buffer solution (pH 6.5) containing 20 mM phosphoric acid and 6.7 mM sodium chloride, 10 mg of α-amylase (Seikagaku Corporation product by using *Bacillus subtills*) and 1 mg of ε-poly-L-lysine were added and dissolved. Then, $10^3$ cells of *Bacillus subtilis* were inoculated to the solution and left at 30° C. for 24 hrs. The solution was filtered through a 0.45 μm membrane filter. To 1 ml of a buffer solution (pH 6.5) containing 20 mM phosphoric acid and 6.7 mM sodium chloride, 0.1 ml of the filtrate and 300 mg of maltose (Wako Pure Chemical Industries Ltd. product) were added. The solution was allowed to react at 60° C. for 24 hrs. After the reaction was completed, the reaction solution was heated in a boiled water to stop the enzyme reaction and then filtered through a 0.45 μm membrane filter. The quantity of glucose in the filtrate was measured by a high speed liquid chromatographic method (column: Showa denko K.K. product, #SC1011). The quantity of glucose thus obtained was 260 mg.

Comparative Example 14

To 1 ml of a buffer solution (pH 6.5) containing 20 mM phosphoric acid and 6.7 mM sodium chloride, 10 mg of α-amylase (saccharification type, Seikagaku Corp. product by using *Bacillus subtills*) were added and dissolved. Then, $10^3$ cells of *Bacillus cereus* were inoculated to the solution and left at 30° C. for 24 hrs. The solution was filtered through a 0.45 μm membrane filter. To 1 ml of a buffer solution (pH 6.5) containing 20 mM phosphoric acid and 6.7 mM sodium chloride, 0.1 ml of the filtrate and 300 mg of maltose (Wako Pure Chemical Industries Ltd. product) were added. The solution was allowed to react at 60° C. for 24 hrs. After the reaction was completed, the reaction solution was heated in a boiled water to stop the enzyme reaction and then filtered through a 0.45 μm membrane filter. The quantity of glucose in the filtrate was measured by a high speed liquid chromatographic method (column: Showa denko K.K. product, #SC1011). No formation of glucose was recognized.

EXAMPLE 16

To 1 ml of a buffer solution (pH 6.5) containing 20 mM phosphoric acid and 6.7 mM sodium chloride, 10 mg of β-amylase (Amano Pharmaceutical Corporation Ltd. product) and 0.1 mg of ε-poly-L-lysine were added and dissolved. Then, $10^3$ cells of *Bacillus cereus* were inoculated to the solution and left at 30° C. for 24 hrs. The solution was filtered through a 0.45 μm membrane filter. To 1 ml of a buffer solution (pH 6.5) containing 20 mM phosphoric acid and 6.7 mM Sodium chloride, 0.1 ml of the filtrate and 10 mg of a soluble starch were added. The solution was allowed to react at 30° C. for 2 days. After the reaction was completed, the reaction solution was heated in a boiled water to stop the enzyme reaction and filtered through a 0.45 μm membrane filter. The quantity of maltose in the filtrate was measured by a dinitrophthallic acid method. The quantity of maltose thus obtained was 7 mg.

Comparative Example 15

To 1 ml of a buffer solution (pH 6.5) containing 20 mM phosphoric acid and 6.7 mM sodium chloride, 10 mg of β-amylase (Amano Pharmaceutical Corporation Ltd. product) were added and dissolved. Then, $10^3$ cells of *Bacillus cereus* were inoculated to the solution and left at 30° C. for 24 hrs. The solution was filtered through a 0.45 μm membrane filter. To 1 ml of a buffer solution (pH 6.5) containing 20 mM phosphoric acid and 6.7 mM sodium chloride, 0.1 ml of the filtrate and 10 mg of a soluble starch were added. The solution was allowed to react at 30° C. for 2 days. After the reaction was completed, the reaction solution was heated in a boiled water to stop the enzyme reaction and then filtered through a 0.45 μm membrane filter. The quantity of maltose in the filtrate was measured by a dinitrophthallic acid method. No formation of maltose was recognized.

EXAMPLE 17

To 1 ml of a buffer solution (pH 6.5) containing 20 mM phosphoric acid and 6.7 mM sodium chloride, 10 mg of mixture of glucoamylase and α-1,6 glucosidase (Amano Pharmaceutical Corporation Ltd. product, "Silverase" [trade name]) and 0.1 mg of ε-poly-L-lysine were added and dissolved. Then, $10^3$ cells of *Bacillus cereus* were inoculated to the solution and left at 30° C. for 24 hrs. The solution was filtered through a 0.45 μm membrane filter. To 1 ml of a buffer solution (pH6.5) containing 20 mM phosphoric acid and 6.7 mM sodium chloride, 0.1 ml of the filtrate and 10 mg of a soluble starch were added. The solution was allowed to react at 30° C. for 2 days. After the reaction was completed, the reaction solution was heated in a boiled water to stop the enzyme reaction and then filtered through a 0.45 μm membrane filter. The quantity of glucose in the filtrate was measured by a high speed liquid chromatographic method (column: Showa denko K.K. product, #SC1011). The quantity of glucosethus obtained was 8 mg.

Comparative Example 16

To 1 ml of a buffer solution (pH 6.5) containing 20 mM phosphoric acid and 6.7 mM sodium chloride, 10 mg of mixture of glucoamylase and α-1,6 glucosidase (Amano Pharmaceutical Corporation Ltd. product, "Silverase" [trade name]) were added and dissolved. Then, $10^3$ cells of *Bacillus cereus* were inoculated to the solution and left at 30° C. for 24 hrs. The solution was filtered through a 0.45 μm membrane filter. To 1 ml of a buffer solution (pH 6.5) containing 20 mM phosphoric acid and 6.7 mM sodium chloride, 0.1 ml of the filtrate and 10 mg of a soluble starch were added. The solution was allowed to react at 30° C. for 2 days. After the reaction was completed, the reaction solution was heated in a boiled water to stop the enzyme reaction and then filtered through a 0.45 μm membrane filter. The quantity of glucose in the filtrate was measured by a high speed liquid chromatographic method (Showa denko K.K. product, #SC1011). No formation of glucose was recognized.

EXAMPLE 18

To 1 ml of a buffer solution (pH 7.5) containing 20 mM phosphoric acid and 6.7 mM sodium chloride, 1 mg of α-glucosidase (Funakoshi K.K. product) and 0.1 mg of ε-poly-L-lysine were added and dissolved. Then, $10^3$ cells of *Bacillus cereus* were inoculated to this solution and left at 30° C. for 24 hrs. The solution was then filtered through a 0.45 μm membrane filter. To 1 ml of a buffer solution (pH 7.5) containing 20 mM phosphoric acid and 6.7 mM sodium chloride, 0.1 ml of the filtrate and 10 mg of a soluble starch were added. The solution was allowed to react at 30° C. for 2 days. After the reaction was completed, the reaction solution was heated in a boiled water to stop the enzyme reaction and then filtered through a 0.45 μm membrane filter. The quantity of maltotriose in the filtrate was measured by a high speed liquid chromatographic method (Showa denko K.K. product, #SC1821). The quantity of maltotriose thus obtained was 1 mg.

Comparative Example 17

To 1 ml of a buffer solution (pH 7.5) containing 20 mM phosphoric acid and 6.7 mM sodium chloride, 1 mg of α-glucosidase (Funakoshi K.K. product) was added and dissolved. Then, $10^3$ cells of *Bacillus cereus* were inoculated to the solution and then left at 30° C. for 24 hrs. The solution was then filtered through a 0.45 μm membrane filter. To 1 ml of a buffer solution (pH 7.5) containing 20 mM phosphoric acid and 6.7 mM sodium chloride, 0.1 ml of the filtrate and 10 mg of a soluble starch were added. The solution was allowed to react at 30° C. for 2 days. After the reaction was completed, the solution was heated in a boiled water to stop the enzyme reaction and then filtered through a 0.45 μm membrane filter. The quantity of maltotriose in the filtrate was measured by a high speed liquid chromatographic method (column: Showa denko K.K. product, #SC1821). No formation of maltotriose was recognized.

EXAMPLE 19

To 1 ml of a buffer solution (pH 6.8) containing 20 mM phosphoric acid and 6.7 mM sodium chloride, 10 mg of xylose isomerase (prepared by using *Bacillus coagulans*) and 0.1 mg of ε-poly-L-lysine were added and dissolved. Then, $10^3$ cells of *Bacillus cereus* were inoculated to the solution and left at 30° C. for 24 hrs. The solution was then filtered through a 0.45 μm membrane filter. To 1 ml of a buffer solution (pH 6.8) containing 20 mM phosphoric acid and 6.7 mM sodium chloride, 0.1 ml of the filtrate and 10 mg of a soluble starch were added. The solution was allowed to react at 30° C. for 2 days. After the reaction was completed, the reaction solution was heated in a boiled water to stop the enzyme reaction and then filtered through a 0.45 μm membrane filter. The quantity of fructose and glucose in the filtrate was measured by a high speed liquid chromatographic method (column: Showa denko K.K. product, #SC1821). The content of fructose thus obtained was 35%.

Comparative Example 18

To 1 ml of a buffer solution (pH 6.8) containing 20 mM phosphoric acid and 6.7 mM sodium chloride, 10 mg of xylose isomerase (prepared by using *Bacillus coagulans*) were added and dissolved. Then, $10^3$ cells of *Bacillus cereus* were inoculated to the solution and left at 30° C. for 24 hrs. The solution was then filtered through a 0.45 μm membrane filter. To 1 ml of a buffer solution (pH 6.8) containing 20 mM phosphoric acid and 6.7 mM sodium chloride, 0.1 ml of the filtrate and 10 mg of a soluble starch were added. The solution was then allowed to react at 30° C. for 2 days. After the reaction was completed, the reaction solution was heated in a boiled water to stop the enzyme reaction and then filtered through a 0.45 μm membrane filter. The quantity of fructose and glucose in the filtrate was measured by a high speed liquid chromatographic method (column: Showa denko K.K. product, #SC1821). No formation of fructose and glucose was recognized.

EXAMPLE 20

To 1 ml of a 20 mM phosphoric acid buffer solution (pH 6.5), 1 mg of cellulase (Worthington Biochemical corp. product by using *Trichoderma reesei*, freeze-dried powder) and 0.5 mg of ε-poly-L-lysine were added and dissolved. Then, $10^3$ cells of *Bacillus cereus* were inoculated to this solution and left at 30° C. for 24 hrs. Then, the solution was filtered through a 0.45 μm membrane filter. To 1 ml of a 50 mM acetic acid buffer solution (pH 5.0), 0.1 ml of the filtrate and 10 mg of Avicel (FMC corp. product) were added and dissolved. The solution was allowed to react at 30° C. for 60 mins. After the reaction was completed, the reaction solution was heated in a boiled water to stop the enzyme reaction and then filtered through a 0.45 μm membrane filter. The quantity of glucose in the filtrate was measured by a high speed liquid chromatographic method (column: Showa denko K.K. product, #SC1011). The quantity of glucosethus obtained was 5 mg.

Comparative Example 19

To 1 ml of a 20 mM phosphoric acid buffer solution (pH 6.5), 1 mg of cellulase (Worthington Biochemical corp. product by using *Trichoderma reesei*, freeze-dried powder) were added and dissolved. Then, $10^3$ cells of *Bacillus cereus* were inoculated to this solution and left at 30° C. for 24 hrs. Then, the solution was filtered through a 0.45 μm membrane filter. To 1 ml of a 50 mM acetic acid buffer solution (pH 5.0), 0.1 ml of the filtrate and 10 mg of Avicel (FMC corp. product) were added and dissolved. The solution was then allowed to react at 30° C. for 60 mins. After the reaction was completed, the reaction solution was heated in a boiled water to stop the enzyme reaction and then filtered through a 0.45 μm membrane filter. The quantity of glucose in the filtrate was measured by a high speed liquid chromatographic method (column: Showa denko K.K. product, #SC1011). No formation of glucose was recognized.

EXAMPLE 21

To 1 ml of a 20 mM phosphoric acid buffer solution (pH 6.5), 1 mg of invertase (Funakoshi K.K. product by using Canadida sp., freeze-dried powder) and 0.5 mg of ε-poly-L-lysine were added and dissolved. Then, $10^3$ cells of *Bacillus cereus* were inoculated to this solution and then left at 30° C. for 24 hrs. The solution was then filtered through a 0.45 μm membrane filter. To 1 ml of a 50 mM acetic acid buffer solution (pH 4.6), 0.1 ml of the filtrate and 10 mg of sucrose (Wako Pure Chemical Industries Ltd. product) were added. The solution was allowed to react at 30° C. for 60 mins. After the reaction was completed, the reaction solution was heated in a boiled water to stop the enzyme reaction and then filtered through a 0.45 μm membrane filter. The quantity of glucose in the filtrate was measured by a high speed liquid chromatographic method (column: Showa denko K.K. product, #SC1011). The quantity of glucose thus obtained was 5 mg.

Comparative Example 20

To 1 ml of a 20 mM phosphoric acid buffer solution (pH 6.5), 1 mg of invertase (Funakoshi K.K. product, Canadida sp., freeze-dried powder) were added and dissolved. Then, $10^3$ cells of *Bacillus cereus* were inoculated to this solution and then left at 30° C. for 24 hrs. The solution was then filtered through a 0.45 μm membrane filter. To 1 ml of a 50 mM acetic acid buffer solution (pH 4.6), 0.1 ml of the filtrate and 10 mg of sucrose (Wako Pure Chemical Industries Ltd. product) were added. The solution was then allowed to react at 30° C. for 60 mins. After the reaction was completed, the reaction solution was heated in a boiled water to stop the enzyme reaction and then filtered through a 0.45 μm membrane filter. The quantity of glucose in the filtrate was measured by a high speed liquid chromatographic method (column: Showa denko K.K. product, #SC1011). No formation of glucose was recognized.

EXAMPLE 22

To 3 ml cyclodextrin glucosyltransferase (Amano Pharmaceutical Corporation Ltd. product, 600U/ml), 25 mg of ε-poly-L-lysine were added and dissolved. Then, $10^3$ cells of *Bacillus cereus* were inoculated to the solution and left at 30° C. for 24 hrs. The solution was then filtered through a 0.45 μm membrane filter. To 50 ml of a buffer solution (pH 7.5) containing 20 mM phosphoric acid and 6.7 mM sodium chloride, 2 ml of the filtrate and 10 g of a soluble starch was added and dissolved. The solution was allowed to react at 65° C. for 40 hrs. After the reaction was completed, the reaction solution was heated in a boiled water to stop the enzyme reaction and then left at 30° C. for 24 hrs. The solution was then filtered through a 0.45 μm membrane filter. The quantity of cyclodextrin in the filtrate was measured by a high speed liquid chromatographic method (column: Showa denko K.K. product, #RSpakC-613). The total quantity of α-, β- and γ-cyclodextrin thus obtained was 7 g.

Comparative Example 21

To 3 ml cyclodextrin glucosyltransferase (Amano Pharmaceutical Corporation Ltd. product, 600U/ml), $10^3$ cells of *Bacillus cereus* were inoculated and then left at 30° C. for 24 hrs. The resulting solution was filtered through a 0.45 μm membrane filter. To 50 ml of a buffer solution (pH 7.5) containing 20 mM phosphoric acid and 6.7 mM sodium chloride, 2 ml of the filtrate and 10 g of a soluble starch was added and dissolved. The solution was then allowed to react at 65° C. for 40 hrs. After the reaction was completed, the reaction solution was heated in a boiled water to stop the enzyme reaction and then left at 30° C. for 24 hrs. The solution was filtered through a 0.45 μm membrane filter. The quantity of cyclodextrin in the filtrate was measured by a high speed liquid chromatographic method (column: Showa denko K.K. product, #RSpakC-613). No formation of cyclodextrin was recognized.

EXAMPLE 23

To 2 ml of a 20 mM tris hydrochloric acid buffer solution (pH 5.0), 20 mg of pectinase (Funakoshi K.K. product by using *Aspergillus niger*, freeze-dried item) and 1 mg of ε-poly-L-lysine were added and dissolved. Then, $10^3$ cells of *Lactobacillus brevis* were inoculated to the solution and then left at 30° C. for 24 hrs. The solution was then filtered through a 0.45 μm membrane filter. Then, 1 ml of the filtrate was mixed with a 20 mM tris hydrochloric acid buffer solution (pH 5.0) dissolving 1 g of polygalacturonic acid (Funakoshi K.K. product), and the resulting solution was allowed to react at 37° C. for 24 hrs. After the reaction was completed, the reaction solution was heated in a boiled water to stop the enzyme reaction and then filtered through a 0.45 μm membrane filter. The quantity of galacturonic acid in the filtrate was measured by a high speed liquid chromatographic method (column: YMC Corp. product, #Diol-120). The quantity of galacturonic acid thus obtained was 450 mg.

Comparative Example 22

To 2 ml of a 20 mM tris hydrochloric acid buffer solution (pH 5.0), 20 mg of pectinase (Funakoshi K.K. product by using *Aspergillus niger*, freeze-dried item) were added and dissolved. Then, $10^3$ cells of *Lactobacillus brevis* were inoculated to the solution and then left at 30° C. for 24 hrs. The solution was then filtered through a 0.45 μm membrane filter. Then, 1 ml of the filtrate was mixed with a 20 mM tris hydrochloric acid buffer solution (pH 5.0) dissolving 1 g of polygalacturonic acid (Funakoshi K.K. product), and the resulting solution was allowed to react at 37° C. for 24 hrs. After the reaction was completed, the reaction solution was heated in a boiled water to stop the enzyme reaction and then filtered through a 0.45 μm membrane filter. The quantity of galacturonic acid in the filtrate was measured by a high speed liquid chromatographic method (column: YMC Corp. product, #Diol-120). No formation of galacturonic acid was recognized.

Since the enzyme reaction stabilizer of the present invention consists of poly-L-lysine or its salt as an effective constituent, this stabilizer has the advantages in that it prevents the deactivation of the enzymes due to the proliferation of included microorganisms in the enzyme reaction solutions, which have been never obtained in the prior art and the decomposition of the reaction products, it has no enzyme reaction inhibition and it can be separated easily from the resulting enzyme reaction solution.

Since the enzyme preservative of the present invention consists of poly-L-lysine as an effective constituent, this preservative has the advantages in that it prevents the deactivation of the enzymes due to the proliferation of included microorganisms in the enzyme solutions or the enzyme preserving solution, it has no enzyme reaction inhibition, it can be easily separated from the reaction products, and it can be preferably used as an enzyme preservative.

What we claim is:

1. A method of preserving enzymes, which comprise the step of:
    dissolving ε-poly-L-lysine having a polymerization degree of about 20 to 40 or its salts in an enzyme solution to thereby prevent the deactivation of enzymes due to the proliferation of microorganisms included in the solution and also to stably preserve the enzymes in said solution, said enzyme solution containing one or more enzyme(s) selected from the group consisting of amylase, cellulase, invertase, pectinase, xylose isomerase and glucosyltransferase.

2. A method of preserving enzymes according to claim 1, wherein ε-poly-L-lysine or its salt is added to the enzyme solution or the enzyme-preserving solution in a quantity of 0.001–10 wt. % based upon the weight of the solution.

3. A preserved enzyme solution containing one or more enzyme(s) selected from the group consisting of amylase, cellulase, invertase, pectinase, xylose isomerase and glucosyltransferase, and ε-poly-L-lysine having a polymerization degree of about 20 to 40 or its salt as a preservative for said enzyme.

4. The preserved enzyme solution according to claim 3, wherein said salt of ε-poly-L-lysine is either the salt of an inorganic acid selected from the group consisting of hydrochloric acid, sulfuric acid, phosphoric acid and hydrobromic acid, or the salt of an organic acid selected from the group consisting of acetic acid, propionic acid, fumaric acid, malic acid and citric acid.

5. A method of carrying out an enzyme reaction comprising the step of:
    reacting one or more enzyme(s) selected from the group consisting of amylase, cellulase, invertase, pectinase, xylose isomerase and cyclodextrin glucosyltransferase in the presence of an enzyme reaction preservative dissolved in a substrate solution to obtain a reaction product, wherein said enzyme reaction preservative comprises ε-poly-L-lysine having a polymerization degree of about 20 to 40 or its salt.

6. A method for carrying out an enzyme reaction according to claim 5, wherein 0.001–10 wt. % of ε-poly-L-lysine or its salt is added to said substrate solution.

* * * * *